(12) United States Patent
Sekimoto

(10) Patent No.: US 11,119,027 B2
(45) Date of Patent: Sep. 14, 2021

(54) MICROBIAL PARTICLE COUNTING SYSTEM AND MICROBIAL PARTICLE COUNTING METHOD

(71) Applicant: RION Co., Ltd., Tokyo (JP)

(72) Inventor: Kazuma Sekimoto, Tokyo (JP)

(73) Assignee: RION Co., Ltd., Tokyo (JP)

( * ) Notice: Subject to any disclaimer, the term of this patent is extended or adjusted under 35 U.S.C. 154(b) by 0 days.

(21) Appl. No.: 16/461,199

(22) PCT Filed: Nov. 7, 2017

(86) PCT No.: PCT/JP2017/040087
§ 371 (c)(1),
(2) Date: May 15, 2019

(87) PCT Pub. No.: WO2018/096920
PCT Pub. Date: May 31, 2018

(65) Prior Publication Data
US 2019/0310179 A1 Oct. 10, 2019

(30) Foreign Application Priority Data

Nov. 22, 2016 (JP) .............................. JP2016-227169
Oct. 20, 2017 (JP) .............................. JP2017-204059

(51) Int. Cl.
*G01T 1/20* (2006.01)
*G01N 15/14* (2006.01)
(Continued)

(52) U.S. Cl.
CPC .............. *G01N 15/14* (2013.01); *C12M 1/34* (2013.01); *C12M 31/02* (2013.01); *C12M 41/36* (2013.01);
(Continued)

(58) Field of Classification Search
CPC ........ G01N 15/14; G01N 15/06; G01N 21/64; G01N 21/65; G01N 2015/1486;
(Continued)

(56) References Cited

U.S. PATENT DOCUMENTS 4,698,308 A * 10/1987 Ikeda ................. G01N 15/1436
250/361 R
2006/0254343 A1 11/2006 Saxena
(Continued)

FOREIGN PATENT DOCUMENTS

JP 2013019894 A 1/2013
JP 2014153199 A 8/2014
(Continued)

OTHER PUBLICATIONS

International Search Report dated Jan. 23, 2018 filed in PCT/JP2017/040087.

*Primary Examiner* — Kiho Kim
(74) *Attorney, Agent, or Firm* — Rankin, Hill & Clark LLP

(57) ABSTRACT

A microbial particle is accurately counted in distinction from a non-microbial particle. A preceding-stage irradiation section 2 irradiates a sample as fluid with ultraviolet light at a preceding stage of a microbial particle counter 1. The ultraviolet light is ultraviolet light having a deep ultraviolet region, the ultraviolet light increasing the fluorescence intensity of a first autofluorescence substance in the microbial particle. The microbial particle counter 1 measures light intensity in a first wavelength range including the fluorescence wavelength of the first autofluorescence substance. In addition, the microbial particle counter 1 measures light intensity in a specific second wavelength range. Further, the microbial particle counter 1 counts the microbial particle in distinction from a non-microbial particle in the fluid based (Continued)

on the measured light intensity in the first wavelength range and the measured light intensity in the specific second wavelength range.

9 Claims, 9 Drawing Sheets

(51) Int. Cl.
    *C12M 1/00*     (2006.01)
    *C12M 1/34*     (2006.01)
    *C12Q 1/06*     (2006.01)
    *G01N 21/65*     (2006.01)
    *G01N 21/64*     (2006.01)
    *G01N 15/06*     (2006.01)

(52) U.S. Cl.
    CPC ............... *C12Q 1/06* (2013.01); *G01N 15/06* (2013.01); *G01N 21/64* (2013.01); *G01N 21/65* (2013.01); *G01N 2015/1486* (2013.01)

(58) Field of Classification Search
    CPC ....... G01N 2015/1488; G01N 15/1456; G01N 2015/0065; C12M 1/34; C12M 31/02; C12M 41/36; C12Q 1/06
    USPC ......................................................... 250/362
    See application file for complete search history.

(56) References Cited

U.S. PATENT DOCUMENTS

| | | | |
|---|---|---|---|
| 2007/0047868 A1* | 3/2007 | Beaulieu | G01N 15/1459 385/12 |
| 2008/0164860 A1* | 7/2008 | Nakajima | G01N 15/1459 324/71.4 |
| 2008/0248965 A1* | 10/2008 | Hansen | G01N 21/59 506/9 |
| 2008/0259321 A1* | 10/2008 | Lea | G01N 33/582 356/213 |
| 2010/0133200 A1 | 6/2010 | Gin | |
| 2011/0204220 A1* | 8/2011 | van Wuijckhuijse | G01N 1/38 250/282 |
| 2011/0291025 A1* | 12/2011 | Fortin | G01N 21/645 250/458.1 |
| 2012/0133936 A1* | 5/2012 | Imai | G01N 15/1429 356/338 |
| 2013/0015362 A1* | 1/2013 | Hooper | G01N 15/1434 250/372 |
| 2013/0052636 A1* | 2/2013 | Verma | C12M 41/46 435/5 |
| 2013/0260417 A1* | 10/2013 | Nijak, Jr. | C12Q 1/04 435/39 |
| 2014/0335557 A1* | 11/2014 | Ichijyo | C02F 1/008 435/34 |
| 2015/0211977 A1* | 7/2015 | Sekimoto | G01N 15/1404 356/338 |
| 2015/0346072 A1 | 12/2015 | Yamasaki et al. | |
| 2015/0346077 A1* | 12/2015 | Sekimoto | G01N 15/1436 250/461.1 |
| 2015/0377786 A1 | 12/2015 | Hosoi et al. | |
| 2017/0205348 A1 | 7/2017 | Obara | |
| 2018/0058998 A1 | 3/2018 | Sekimoto | |
| 2018/0246089 A1* | 8/2018 | Chou | G01N 1/2813 |

FOREIGN PATENT DOCUMENTS

| | | |
|---|---|---|
| JP | 2015108549 A | 6/2015 |
| JP | 2016080673 A | 5/2016 |
| JP | 6240280 B1 | 11/2017 |
| WO | 2016056405 A1 | 4/2016 |
| WO | 2016093305 A1 | 6/2016 |

* cited by examiner

FIG. 9
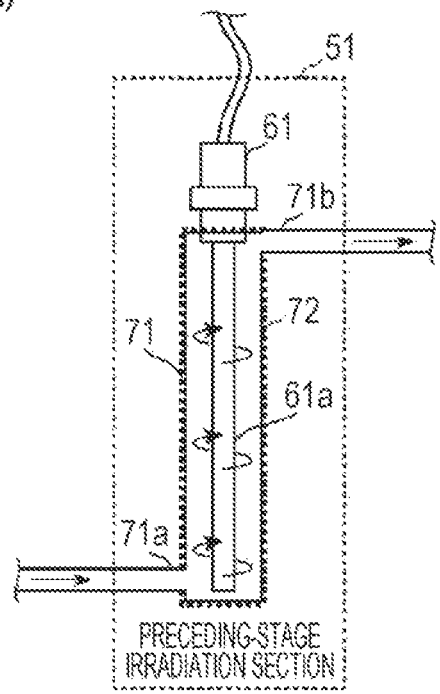
(A)
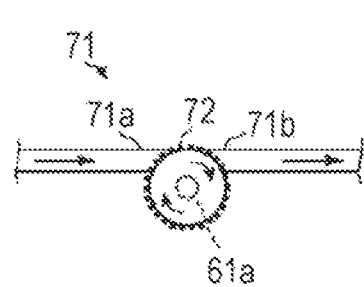
(B)

MICROBIAL PARTICLE COUNTING SYSTEM AND MICROBIAL PARTICLE COUNTING METHOD

TECHNICAL FIELD

The present invention relates to a microbial particle counting system and a microbial particle counting method.

BACKGROUND ART

In a certain liquid fluorescence detection device, liquid in a cell is irradiated with excitation light. Then, light with a longer first fluorescence wavelength band than that of Raman scattered light and light with a shorter second fluorescence wavelength band than that of the Raman scattered light are detected. In a case where light intensity in the first fluorescence wavelength band is higher than light intensity in the second fluorescence wavelength band, it is determined that a microbial particle is contained in the liquid. In a case where the light intensity in the second fluorescence wavelength band is higher than the light intensity in the first fluorescence wavelength band, it is determined that a non-microbial particle is contained in the liquid (see, e.g., Patent Literature 1).

On the other hand, in a certain microbial particle counter, a sample is, as preprocessing for microbial particle measurement, irradiated with ultraviolet light having an UV-C wavelength range. Thus, the autofluorescence intensity of a microbial particle due to excitation light is increased. Of such autofluorescence, fluorescence in a single specific wavelength range is detected. By comparison between the light intensity of the detected fluorescence and a threshold, the microbial particle is detected (see, e.g., Patent Literature 2).

CITATION LIST

Patent Literature

PATENT LITERATURE 1: JP-A-2016-080673
PATENT LITERATURE 2: JP-A-2014-153199

SUMMARY OF THE INVENTION

Problems to be Solved by the Invention

However, fluorescence of an individual microbial particle is weak. Thus, sometimes, the fluorescence is buried in background noise. In that case, the liquid fluorescence detection device of Patent Literature 1 can detect neither an individual microbial particle nor fluorescence thereof. Moreover, as illustrated in FIG. 2 (ultraviolet light not irradiated), a magnitude relationship between fluorescence intensity in the first fluorescence wavelength band and fluorescence intensity in the second fluorescence wavelength band is sometimes inverted depending on the type of bacterium.

On the other hand, in the microbial particle counter of Patent Literature 2, a non-microbial particle emitting fluorescence due to the excitation light irradiating the microbial particle is sometimes contained in the sample. In this case, the microbial particle cannot be detected in distinction from the non-microbial particle in some cases.

Thus, it is sometimes difficult for the above-described technique to accurately count the microbial particle in distinction from the non-microbial particle.

The present invention has been made in view of the above-described problems. That is, the present invention is intended to provide a microbial particle counting system and a microbial particle counting method for accurately counting a microbial particle in distinction from a non-microbial particle.

Solution to the Problems

A microbial particle counting system according to the present invention includes a microbial particle counter configured to irradiate fluid with excitation light to detect autofluorescence of a microbial particle in the fluid and count the microbial particle in the fluid, and a preceding-stage irradiation section provided at a preceding stage of the microbial particle counter and configured to irradiate a sample as the fluid with ultraviolet light. And the ultraviolet light is ultraviolet light having a deep ultraviolet region, the ultraviolet light increasing fluorescence intensity of a first autofluorescence substance in the microbial particle, and the microbial particle counter measures light intensity in a first wavelength range including a fluorescence wavelength of the first autofluorescence substance and light intensity in a specific second wavelength range, and counts the microbial particle in distinction from a non-microbial particle in the fluid based on the measured light intensity in the first wavelength range and the measured light intensity in the specific second wavelength range.

A microbial particle counting method according to the present invention includes a step of irradiating a sample with ultraviolet light at a preceding stage of a microbial particle counter, and a step of causing the sample as fluid irradiated with the ultraviolet light to flow into the microbial particle counter and irradiating the fluid with excitation light in the microbial particle counter, thereby detecting autofluorescence of a microbial particle in the fluid and counting the microbial particle in the fluid. And the ultraviolet light is ultraviolet light having a deep ultraviolet region, the ultraviolet light increasing fluorescence intensity of a first autofluorescence substance in the microbial particle, and the microbial particle counter measures light intensity in a first wavelength range including a fluorescence wavelength of the first autofluorescence substance and light intensity in a specific second wavelength range, and counts the microbial particle in distinction from a non-microbial particle in the fluid based on the measured light intensity in the first wavelength range and the measured light intensity in the specific second wavelength range.

Effects of the Invention

According to the present invention, the microbial particle is accurately counted in distinction from the non-microbial particle.

BRIEF DESCRIPTION OF THE DRAWINGS

FIG. 9 illustrates views of one example of a preceding-stage irradiation section 51 in a microbial particle counting system according to a fifth embodiment of the present invention.

DESCRIPTION OF EMBODIMENTS

Hereinafter, an embodiment of the present invention will be described with reference to the drawings.

First Embodiment

Figure 1:
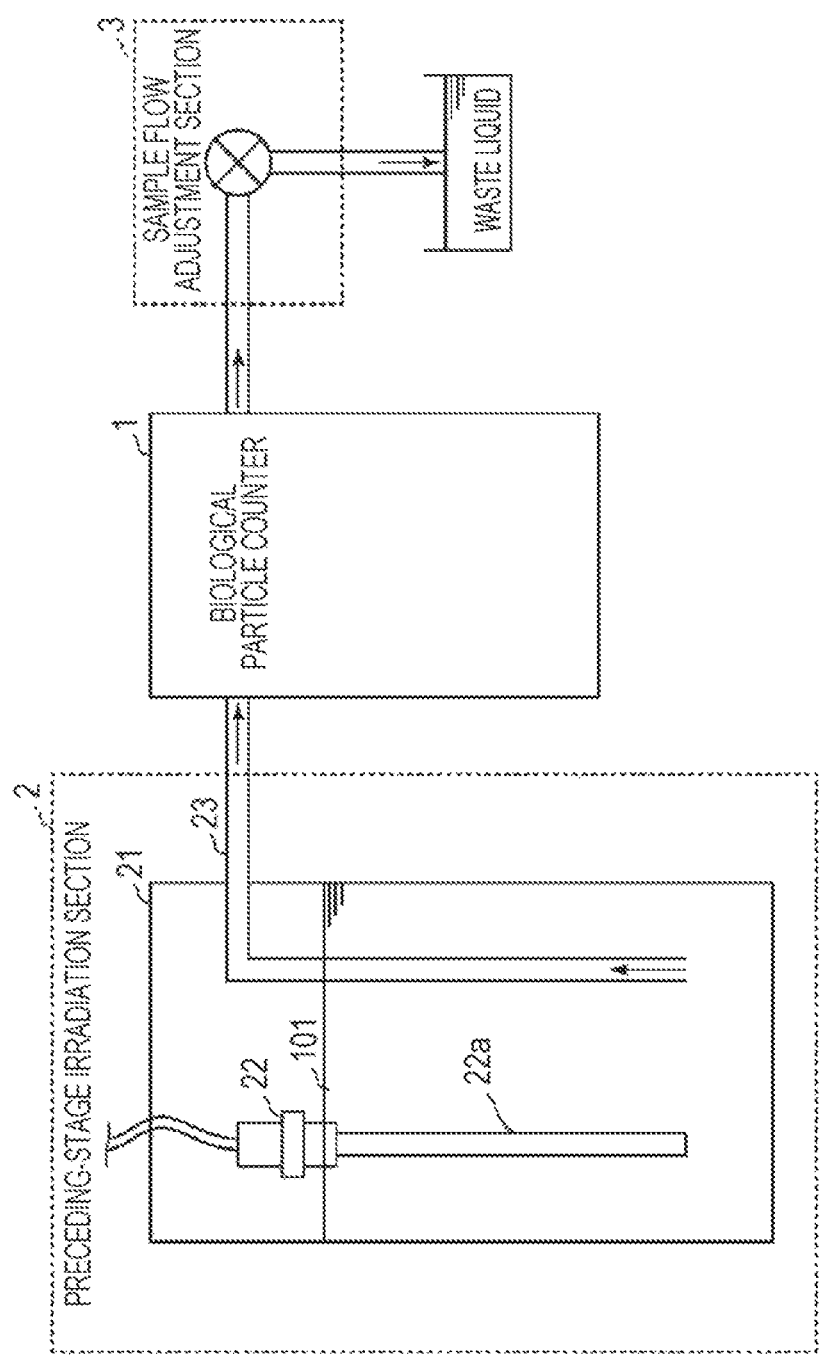
FIG. 1 illustrates a block diagram of a structure of a microbial particle counting system according to a first embodiment of the present invention.

FIG. 1 illustrates a block diagram of a structure of a microbial particle counting system according to a first embodiment of the present invention. The microbial particle counting system according to the first embodiment includes a microbial particle counter 1, a preceding-stage irradiation section 2, and a sample flow adjustment section 3.

The microbial particle counter 1 irradiates fluid as a sample with measurement light (excitation light). Moreover, the microbial particle counter 1 detects autofluorescence of a microbial particle in the fluid, thereby counting the microbial particle in the fluid. The microbial particle counter 1 can count a microbial particle with a size of 0.1 μm to hundreds of μm, for example. Specifically, the microbial particle targeted for counting is a bacterium, a yeast, or a fungus, for example. A cell of the microbial particle contains a specific autofluorescence substance (e.g., a flavin group such as riboflavin) emitting autofluorescence. Thus, such autofluorescence is detected so that the microbial particle can be counted.

The preceding-stage irradiation section 2 is provided at a preceding stage of the microbial particle counter 1. The preceding-stage irradiation section 2 irradiates, with ultraviolet light having a specific wavelength, the sample as the fluid flowing into the microbial particle counter 1.

The sample flow adjustment section 3 adjusts, with a pump, a valve, etc., the flow rate of the sample (i.e., the sample flowing into the microbial particle counter 1) flowing out of the microbial particle counter 1. Moreover, the sample flow adjustment section 3 discharges the sample after counting of the microbial particle by the microbial particle counter 1 has completed.

As illustrated in FIG. 1, the microbial particle counting system according to the first embodiment is a batch counting system. The preceding-stage irradiation section 2 includes a storage section 21 having a container configured to store sample water 101, a light source 22 configured to emit the above-mentioned ultraviolet light toward the sample water 101 in the storage section 21, and a flow passage section 23 configured to supply, as the fluid, the sample water 101 from the storage section 21 to the microbial particle counter 1.

Note that in a case where the storage section 21 is made of a material transmitting the ultraviolet light from the light source 22, a shielding material configured to shield the ultraviolet light is arranged at the outer periphery of the storage section 21 to avoid leakage of the ultraviolet light from the light source 22 to the outside. Preferably, a material on which the ultraviolet light is reflectable, such as aluminum or polytetrafluoroethylene (PTFE), is used as the shielding material.

The light source 22 is arranged inside the container of the storage section 21. The light source 22 has a light emitting section 22a configured to emit the above-mentioned ultraviolet light. For example, the light source 22 irradiates the sample water 101 with the above-mentioned ultraviolet light with the entirety of the light emitting section 22a being in the sample water 101 in the storage section 21. Note that a stirrer configured to stir the sample such that the sample water 101 in the storage section 21 is evenly irradiated with the ultraviolet light may be provided at the preceding-stage irradiation section 2.

The ultraviolet light irradiated at the preceding-stage irradiation section 2 is ultraviolet light with a deep ultraviolet region (equal to or less than 300 nm, preferably equal to or less than 254 nm, and more preferably equal to or less than 185 nm), the ultraviolet light increasing the fluorescence intensity of the specific autofluorescence substance in the microbial particle targeted for counting. In the first embodiment, sterilizing light with 254 nm is used as the ultraviolet light.

Figure 2:
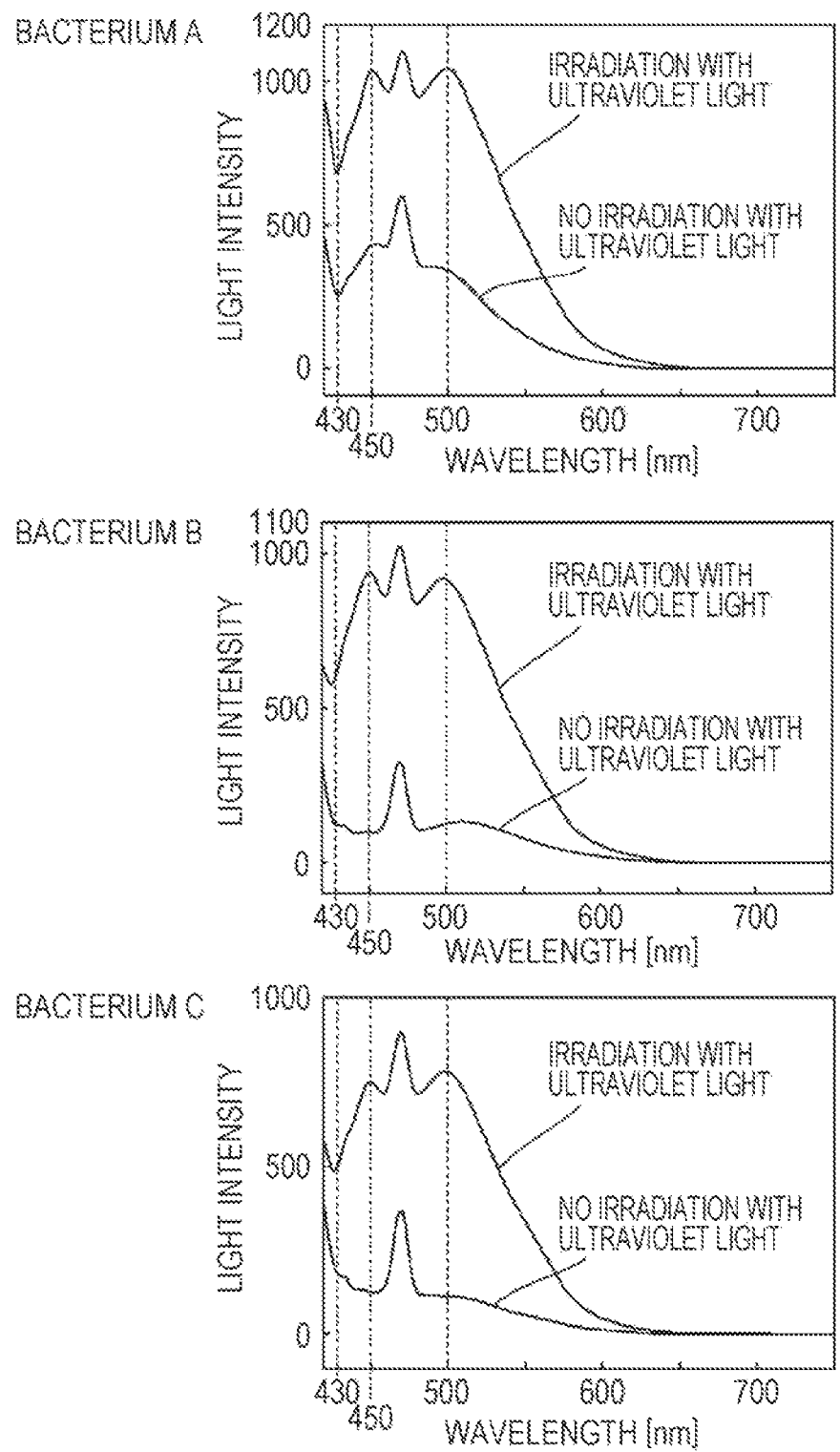
FIG. 2 illustrates graphs of a change in a fluorescence spectrum due to ultraviolet light irradiation to specific bacteria A, B, C.
Figure 3:
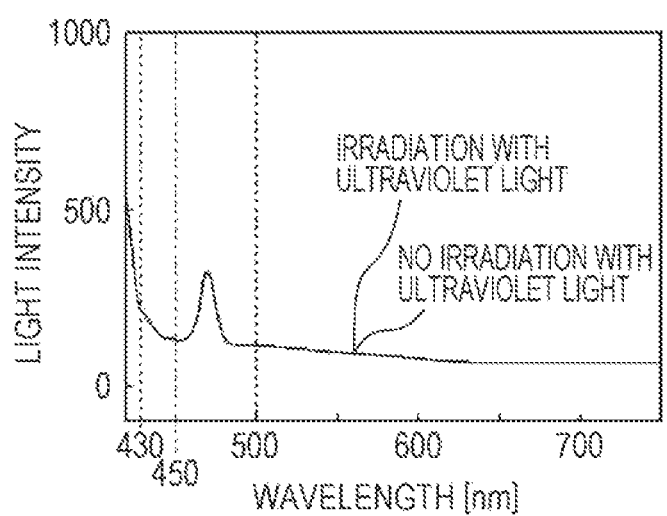
FIG. 3 illustrates a graph of a fluorescence spectrum of a non-microbial particle (a silicon particle)
Figure 4:
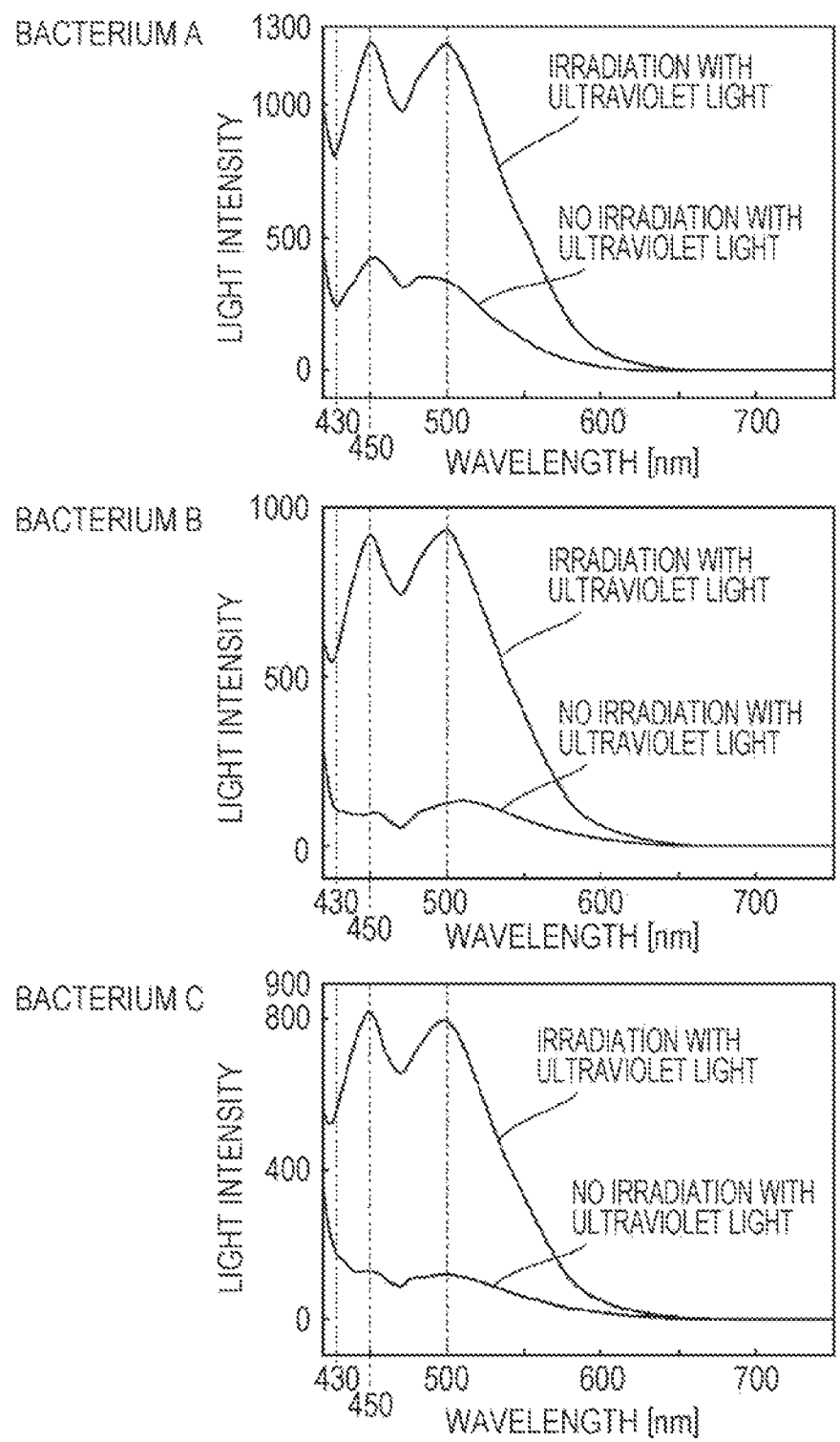
FIG. 4 illustrates graphs of a change in a fluorescence spectrum (excluding a Raman scattered light component) due to ultraviolet light irradiation to the specific bacteria A, B, C.
Figure 5:
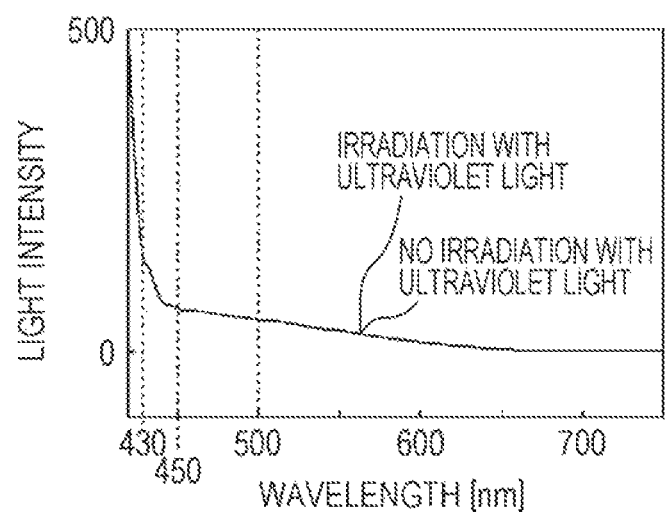
FIG. 5 illustrates a graph of a fluorescence spectrum (excluding the Raman scattered light component) of the non-microbial particle (the silicon particle)

FIG. 2 illustrates graphs of a change in a fluorescence spectrum due to ultraviolet light irradiation to specific bacteria A, B, C. FIG. 3 illustrates a graph of a fluorescence spectrum of a non-microbial particle (a silicon particle). FIG. 4 illustrates graphs of a change in a fluorescence spectrum (excluding a Raman scattered light component) due to ultraviolet light irradiation to the specific bacteria A, B, C. FIG. 5 illustrates a graph of a fluorescence spectrum (excluding the Raman scattered light component) of the non-microbial particle (the silicon particle).

The bacterium A described herein is a *Pseudomonas* bacterium. The bacterium B is a *Sphingomonas* bacterium. The bacterium C is a *Methylobacterium* bacterium.

FIGS. 2 to 5 show measurement results such as a fluorescence spectrum for excitation light with 405 nm in each of a case where irradiation with the above-mentioned ultraviolet light having the deep ultraviolet region has been experimentally performed and a case where such irradiation has not been performed. Note that light intensity distribution illustrated in FIGS. 2 to 5 includes a scattered light component in addition to the fluorescence spectrum. A light intensity peak at about 465 nm in FIGS. 2 and 3 is caused by the Raman scattered light component. The fluorescence spectrum excluding the Raman scattered light component is illustrated in FIGS. 4 and 5. Moreover, the peak wavelength of the excitation light in the case of FIGS. 2 to 5 is 405 nm. A wavelength range of less than 430 nm includes the scattered light component (or an excitation light component).

As illustrated in FIGS. 2 and 4, in any of the fluorescence spectra of the bacteria A, B, C, peaks are formed at about 450 nm and about 500 nm due to ultraviolet light irradiation described above. Note that in FIGS. 2 and 4, the light intensity of the scattered light component (or the excitation light component) is not increased due to ultraviolet light irradiation described above. However, due to the slopes and edges corresponding to the peaks at about 450 nm and about 500 nm in the fluorescence spectrum, light intensity in a wavelength range of less than 430 nm is also increased due to ultraviolet light irradiation described above.

The wavelength of the autofluorescence shows distribution unique to the autofluorescence substance. For example, autofluorescence spectra of the riboflavin as the flavin group and coenzyme flavin adenine dinucleotide (FAD) thereof have peaks at a wavelength of about 520 nm. Moreover, an autofluorescence spectrum of a folate group (folate and derivatives thereof) has a peak at a wavelength of about 450 nm.

Thus, it is assumed that the above-mentioned peak at about 500 nm is derived from the flavin group having the fluorescence peak wavelength at about 520 nm. It is assumed that the above-mentioned peak at about 450 nm is derived from the folate group having the fluorescence peak wavelength at about 450 nm.

On the other hand, the fluorescence intensity of the non-microbial particle is not increased due to ultraviolet light irradiation described above. Regardless of the presence or absence of ultraviolet light irradiation, the fluorescence spectrum of the non-microbial particle does not change as illustrated in FIGS. 3 and 5.

As described above, the fluorescence intensity of the specific autofluorescence substance such as the flavin group or the folate group is increased due to ultraviolet light irradiation at the preceding-stage irradiation section 2.

Figure 6:
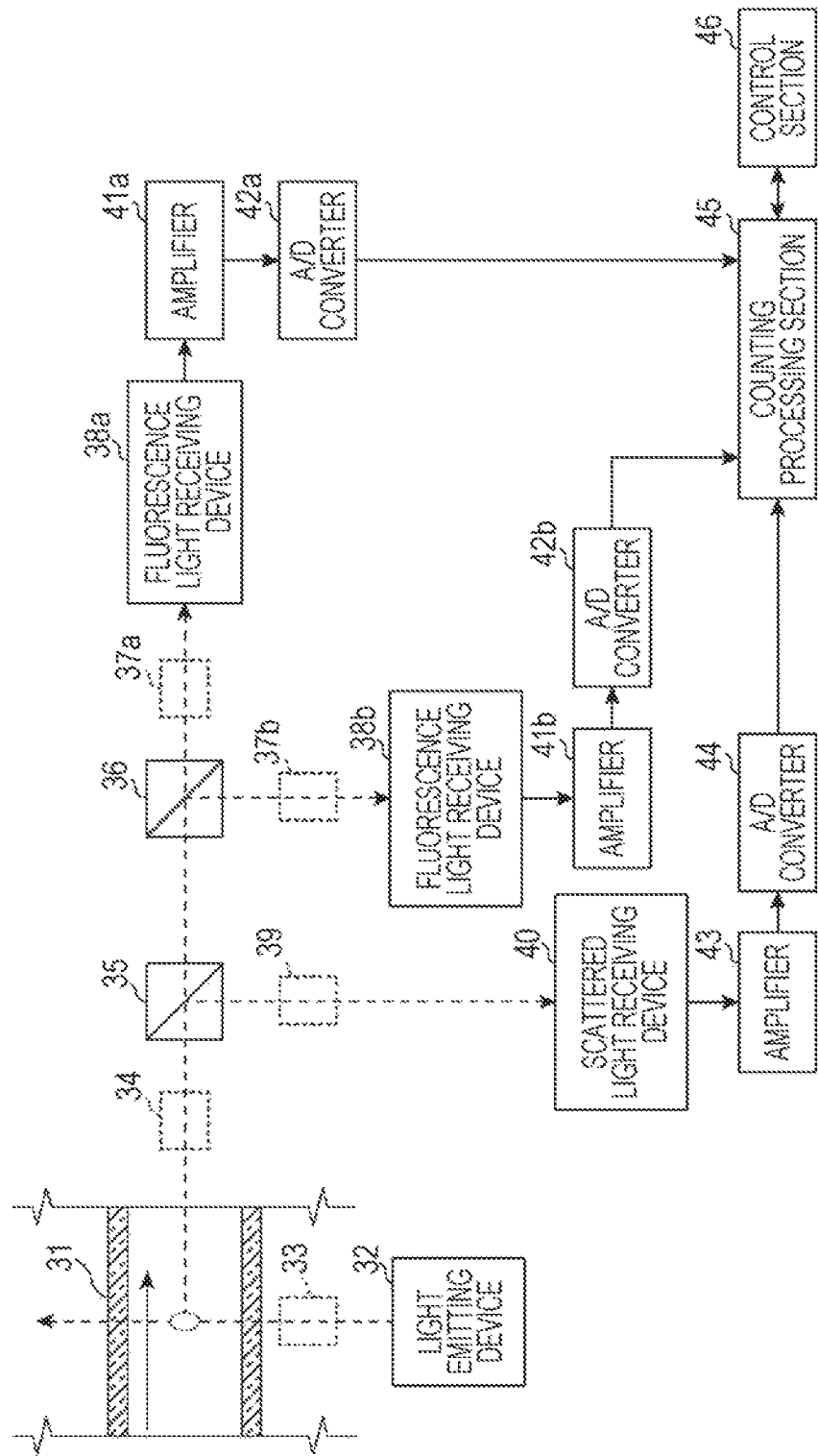
FIG. 6 illustrates a block diagram of a structure of a microbial particle counter 1 of FIG. 1.

Next, a structure of the microbial particle counter 1 will be described. FIG. 6 illustrates a block diagram of the structure of the microbial particle counter 1 of FIG. 1. As illustrated in FIG. 6, the microbial particle counter 1 includes a flow cell 31, a light emitting device 32, an irradiation optical system 33, a detection optical system 34, a scattered light selection optical element 35, a fluorescence selection optical element 36, light receiving optical systems 37a, 37b, fluorescence light receiving devices 38a, 38b, a light receiving optical system 39, and a scattered light receiving device 40.

The flow cell 31 forms a flow passage for the fluid containing the microbial particle targeted for counting. The flow cell 31 includes a tubular transparent member which can form the flow passage, such as synthetic quartz or sapphire. The flow cell 31 has a hollow and quadrangular prism shape.

The light emitting device 32 includes a light source (e.g., a semiconductor light emitting element such as a laser diode) configured to emit light (laser light in this case) with a predetermined wavelength. The light source emits the excitation light for exciting the autofluorescence substance in the microbial particle. The excitation light has a wavelength unique to the autofluorescence substance in a range from an ultraviolet light region to a green visible light region, for example.

For example, an excitation absorption spectrum of the riboflavin has peaks at about 375 nm and about 450 nm. Thus, laser light having a wavelength within a range of 330 nm to 500 nm is used as excitation light for the riboflavin, for example. For example, in the first embodiment, laser light with 405 nm is used.

The irradiation optical system 33 irradiates the fluid flowing in the flow passage with the excitation light from a direction (a perpendicular direction in this case) different from a fluid traveling direction in the flow passage of the flow cell 31. The irradiation optical system 33 includes, for example, various lenses (e.g., a collimater lens, a biconvex lens, and a cylindrical lens), adjusts the laser light from the light emitting device 32 to be parallel beams of light, and irradiates, with the parallel beams of light as the excitation light, the fluid in the flow passage. When the fluid flowing in the flow passage of the flow cell 31 is irradiated with the excitation light, a detection region is formed. Note that a beam damper (a beam trap) configured to shield the excitation light transmitted by the flow cell 31 may be arranged.

The detection optical system 34 causes the scattered light and the fluorescence from the particle in the flow passage due to irradiation with the above-mentioned excitation light to enter a predetermined incidence surface of the scattered light selection optical element 35. For example, a condensing lens may be used for the detection optical system 34. Alternatively, an optical system having a pinhole for shielding background light and condensing lenses each arranged on the front and back sides of the pinhole may be used.

In a case where the microbial particle has been irradiated with the excitation light, the scattered light and the autofluorescence from the microbial particle enter the predetermined incidence surface of the scattered light selection optical element 35. Note that there are some cases where the non-microbial particle emitting fluorescence is contained in the fluid in addition to the autofluorescence from the microbial particle as the target for counting. In this case, when the non-microbial particle is irradiated with the excitation light, the non-microbial particle also emits the fluorescence.

Note that in a case where the sample is water as liquid, Raman scattered light from the water in response to the excitation light also enters the scattered light selection optical element 35 through the detection optical system 34. For example, in a case where the excitation light has a wavelength of 405 nm, the Raman scattered light from the water has a peak wavelength of 465 nm.

Moreover, in this embodiment, the excitation light enters the flow passage of the flow cell 31 from a direction different from the optical axis of the detection optical system 34. Thus, side-scattered light enters the scattered light selection optical element 35 through the detection optical system 34.

The scattered light selection optical element 35 is an optical element (e.g., a dichroic mirror). This optical element transmits light with a range of fluorescence wavelengths longer than the wavelength of the scattered light having the same wavelength as that of the excitation light, and reflects light with a range of wavelengths of the scattered light from the particle (i.e., a range of wavelengths of the excitation light).

The fluorescence selection optical element 36 is an optical element configured to separate light having a specific wavelength range and light having another wavelength range from the light transmitted by the scattered light selection optical element 35. The fluorescence selection optical element 36 is an optical element (e.g., a dichroic mirror) configured to transmit the light having the specific wavelength range and reflect the light having another wavelength range.

This specific wavelength range includes a first wavelength range targeted for measurement of the fluorescence intensity. Moreover, another wavelength range includes a specific second wavelength range targeted for measurement of the fluorescence intensity.

The first wavelength range includes the fluorescence wavelength of the specific autofluorescence substance.

In the first embodiment, the above-mentioned first wavelength range in the microbial particle counter 1 includes the fluorescence wavelength of the flavin group (the riboflavin, the flavin adenine dinucleotide (FAD), etc.) as the specific autofluorescence substance.

Note that the fluorescence of the autofluorescence substance normally has relatively-broad wavelength distribution. For this reason, the first wavelength range does not necessarily include a known peak wavelength unique to the specific autofluorescence substance. In this case, the first wavelength range may be set to include the wavelength at the local maximum value of the fluorescence spectrum of the microbial particle (the bacterium) closest to the known peak wavelength of the specific autofluorescence substance. That is, due to, e.g., influence of other autofluorescence substances, the local maximum value of the fluorescence spectrum of the microbial particle (the bacterium) is sometimes shown at another wavelength around the peak wavelength unique to the specific autofluorescence substance. In this case, the first wavelength range may be a wavelength range having a predetermined width and including the wavelength at the local maximum value of the fluorescence spectrum closest to the fluorescence peak wavelength of the autofluorescence substance.

The fluorescence peak wavelength of the flavin group as described herein is about 520 nm. However, as illustrated in FIGS. 2 and 4, the local maximum value of the fluorescence spectrum of the microbial particle (the bacterium) due to ultraviolet light irradiation is shown at about 500 nm, which is close to 520 nm. Thus, in the first embodiment, the first wavelength range is a wavelength range having a predetermined width (e.g., ±10 nm) and including a wavelength value of 500 nm at the local maximum value. Note that the first wavelength range may include the fluorescence peak wavelength of the flavin group (about 520 nm), needless to say.

On the other hand, in the first embodiment, the second wavelength range is a predetermined wavelength range between the wavelength (405 nm in the first embodiment) of the above-mentioned excitation light and the first wavelength range, the predetermined wavelength range not including the fluorescence peak wavelength of an autofluorescence substance, whose fluorescence intensity is increased by the ultraviolet light irradiated at the preceding-stage irradiation section 2, in the microbial particle. Further, in a case where the sample contains water, the second wavelength range is set to between the wavelength of the excitation light and the peak wavelength of the Raman scattered light such that the peak wavelength of the Raman scattered light is not included in the second wavelength range.

In the first embodiment, the folate group has a fluorescence peak wavelength of about 450 nm. Moreover, the local maximum value of the fluorescence spectrum of the microbial particle (the bacterium) due to ultraviolet light irradiation is also shown at 450 nm. Thus, as illustrated in FIGS. 2 and 4, the second wavelength range is a wavelength range having a predetermined width (e.g., ±10 nm) and including 430 nm but including neither the fluorescence peak wavelength of the folate group nor the wavelength of the Raman scattered light.

The light receiving optical system 37a condenses, by a condensing lens group, light on the fluorescence light receiving device 38a, the light transmitted the fluorescence selection optical element 36 and having the specific wavelength range (i.e., the wavelength range including the first wavelength range). The light receiving optical system 37b condenses, by a condensing lens group, light on the fluorescence light receiving device 38b, the light having been reflected on the fluorescence selection optical element 36 and having another wavelength range (i.e., the wavelength range including the second wavelength range).

Note that one or both of the light receiving optical systems 37a, 37b may have a long-pass filter, a bandpass filter, or a short-pass filter. According to the intensity of the Raman scattered light entering through the scattered light selection optical element 35 and the fluorescence selection optical element 36, these filters shield the Raman scattered light, and transmit the light having the above-mentioned wavelength range.

The fluorescence light receiving devices 38a, 38b each have semiconductor light receiving elements such as photodiodes or phototransistors or photomultiplier tubes. Each of the fluorescence light receiving devices 38a, 38b receives the condensed light at the semiconductor light receiving element or the photomultiplier tube and converts the received light into an electrical signal, thereby outputting the electrical signal according to the intensity of the received light.

The light receiving optical system 39 condenses, by a condensing lens group, light (the scattered light) on the scattered light receiving device 40, the light having been reflected on the scattered light selection optical element 35. The scattered light receiving device 40 has a semiconductor light receiving element such as a photodiode or a phototransistor or a photomultiplier tube. The semiconductor light receiving element or the photomultiplier tube receives the condensed scattered light. The received scattered light is converted into an electrical signal by the scattered light receiving device 40. The scattered light receiving device 40 outputs the electrical signal according to the intensity of the received light.

Further, the microbial particle counter 1 includes amplifiers 41a, 41b, A/D converters 42a, 42b, an amplifier 43, an A/D converter 44, a counting processing section 45, and a control section 46. The amplifiers 41a, 41b each amplify the voltages of the electrical signals from the fluorescence light receiving devices 38a, 38b at a predetermined amplification factor. The A/D converters 42a, 42b each convert the amplified electrical signals into digital signals. The amplifier 43 amplifies the voltage of the electrical signal from the scattered light receiving device 40 at a predetermined amplification factor. The A/D converter 44 converts the amplified electrical signal into a digital signal.

The counting processing section 45 is a digital processing circuit configured to count (e.g., for each particle size classification) the microbial particle passing through a measurement region based on the digital signals (a first measurement signal and a second measurement signal) corresponding to the fluorescence and output from the A/D converters 42a, 42b and the digital signal (a third measurement signal) corresponding to the scattered light and output from the A/D converter 44.

As described above, the microbial particle counter 1 (a) measures the light intensity in the above-mentioned first wavelength range and the light intensity in the above-mentioned second wavelength range by means of a fluorescence measurement system such as the fluorescence selection optical element 36, the light receiving optical systems 37a, 37b, and the fluorescence light receiving devices 38a, 38b, and (b) counts, by means of the counting processing section 45, the microbial particle in distinction from the non-microbial particle in the fluid based on the measured light intensity in the first wavelength range and the measured light intensity in the second wavelength range.

In the first embodiment, the counting processing section 45 determines whether or not the pulse height value of the first measurement signal (the digital signal from the A/D converter 42a) corresponding to the fluorescence in the first wavelength range is greater than that of the second measurement (the digital signal form the A/D converter 42b)

corresponding to the fluorescence in the second wavelength range when both of the value of the first measurement signal and the value of the second measurement signal exceed a predetermined threshold. In a case where the pulse height value of the first measurement signal is greater than that of the second measurement signal, it is determined that a single microbial particle has been detected, and the microbial particle is counted. This threshold corresponds to the upper limit level of background noise. That is, the threshold is set such that the background noise level does not exceed the threshold. Further, this threshold is set to a value corresponding to the increment of the light intensity in the first wavelength range and the increment of the light intensity in the second wavelength range due to ultraviolet light irradiation described above. That is, as the increment of the light intensity in the first wavelength range and the increment of the light intensity in the second wavelength range increase, this threshold is set higher than the upper limit level of the background noise. Note that these increments are specified in advance by experiment, for example.

On the other hand, in the first embodiment, in a case where at least one of the value of the first measurement signal or the value of the second measurement signal does not exceed the predetermined threshold, the counting processing section 45 does not determine that the microbial particle has been detected, and no microbial particle is counted. Further, in a case where both of the value of the first measurement signal and the value of the second measurement signal exceed the predetermined threshold, but the pulse height value of the first measurement signal is equal to or less than that of the second measurement signal, the counting processing section 45 does not determine that the microbial particle has been detected, and no microbial particle is counted.

That is, in the first embodiment, the microbial particle counter 1 counts the microbial particle in a case where the measured light intensity in the first wavelength range is higher than the measured light intensity in the second wavelength range. In the case of the microbial particle, the light intensity in the first wavelength range reaches, as illustrated in FIGS. 2 and 4, higher than the light intensity in the second wavelength range due to ultraviolet light irradiation at the preceding-stage irradiation section 2 regardless of the type of microbial particle. Thus, the microbial particle is reliably counted as the microbial particle. On the other hand, in the case of the non-microbial particle, the fluorescence intensity thereof is low. Thus, the fluorescence intensity is, as described above, not increased even by ultraviolet light irradiation at the preceding-stage irradiation section 2. Thus, at least one of the values of the first measurement signal and the second measurement signal is less likely to exceed the predetermined threshold. As a result, the non-microbial particle is less likely to be counted as the microbial particle. Note that in the case of the non-microbial particle, even when the values of the first measurement signal and the second measurement signal exceed the predetermined threshold, the light intensity in the first wavelength range is lower than the light intensity in the second wavelength range. Thus, the non-microbial particle is not counted as the microbial particle.

Further, the counting processing section 45 specifies the size of the detected microbial particle based on the pulse height value of the third measurement signal corresponding to the scattered light.

Note that in the case of also counting the non-microbial particle, when no microbial particle has been detected, but the pulse height value of the measurement signal corresponding to the scattered light exceeds the predetermined threshold, it may be determined that a single non-microbial particle has been detected.

The control section 46 controls an internal device such as the counting processing section 45. That is, the control section 46 outputs, as measurement data, a measurement result received from the counting processing section 45, or display, as a graph etc., the measurement result on a display device (not shown).

Next, counting of the microbial particle in the microbial particle counting system according to the first embodiment will be described.

The microbial particle counting system according to the first embodiment employs a batch method. Thus, as illustrated in FIG. 1, a certain amount of sample water 101 enters the storage section 21 in every measurement. Next, the light source 22 is turned on. Then, the sample water 101 is irradiated with the above-mentioned ultraviolet light. Accordingly, the microbial particle in the sample water 101 is also irradiated with the above-mentioned ultraviolet light with predetermined intensity for predetermined time. Due to such ultraviolet light irradiation the intensity of the autofluorescence, e.g., the autofluorescence of the flavin group in the microbial particle, increases in the succeeding-stage microbial particle counter 1.

After the above-mentioned ultraviolet light has been irradiated for the predetermined time, the light source 22 is turned off. Then, the sample water 101 flows into the microbial particle counter 1 by the sample flow adjustment section 3. Thereafter, the microbial particle counter 1 starts counting the microbial particle. The microbial particle counter 1 counts the microbial particle in the sample water 101 as the fluid.

In the microbial particle counter 1, the light emitting device 32 and the irradiation optical system 33 irradiate the sample water 101 with the excitation light.

Then, the first measurement signal indicating the light intensity in the first wavelength range and the second measurement signal indicating the light intensity in the second wavelength range are output to the counting processing section 45 by the fluorescence measurement system including the fluorescence selection optical element 36, the light receiving optical systems 37a, 37b, the fluorescence light receiving devices 38a, 38b, the amplifiers 41a, 41b, and the A/D converters 42a, 42b. Meanwhile, the third measurement signal indicating the light intensity in the wavelength range including the wavelength of the excitation light is output to the counting processing section 45 by a scattered light measurement system including the scattered light selection optical element 35, the light receiving optical system 39, the scattered light receiving device 40, the amplifier 43, and the A/D converter 44.

Figure 7:
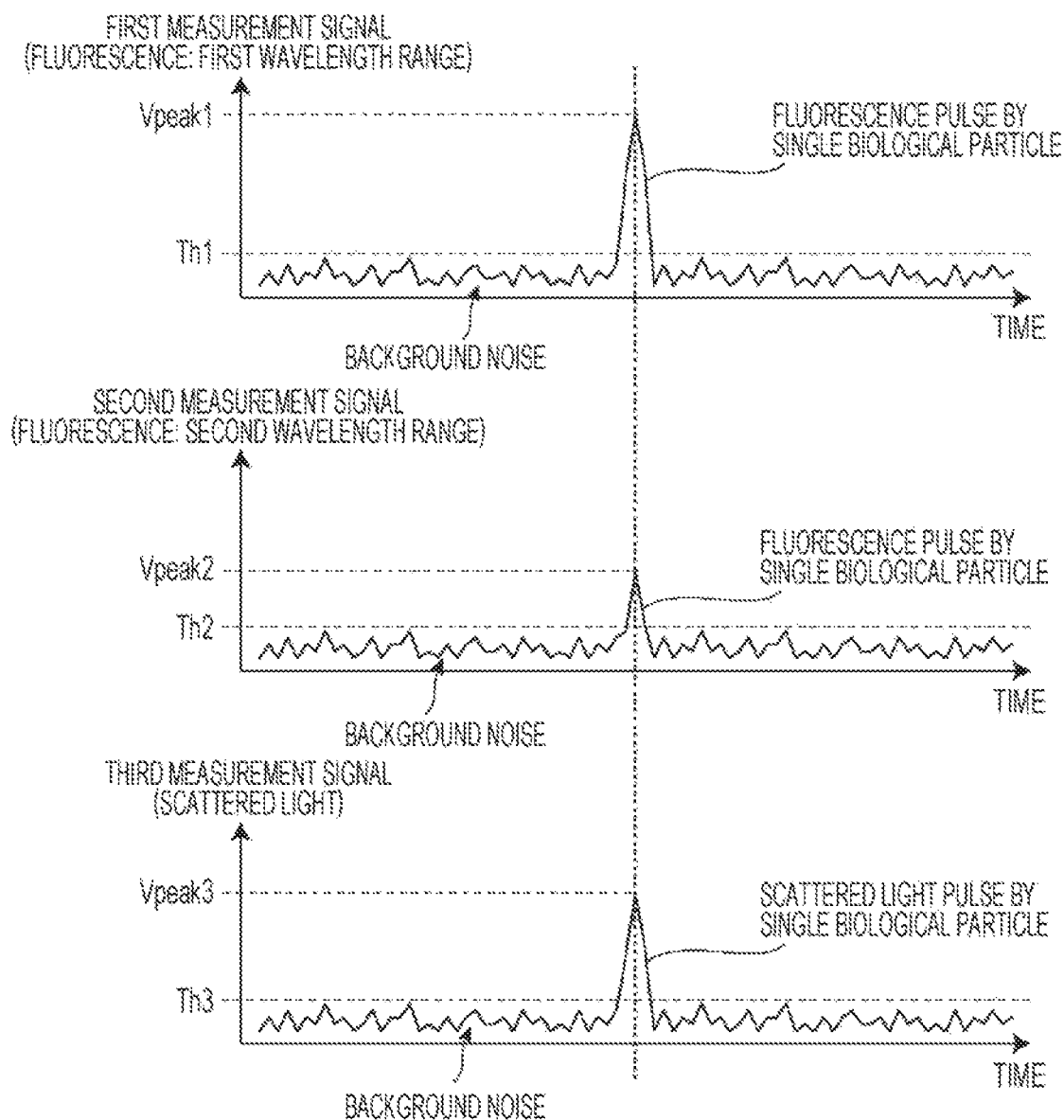
FIG. 7 illustrates timing charts for describing a first measurement signal, a second measurement signal, and a third measurement signal in the first embodiment.

FIG. 7 illustrates timing charts for describing the first measurement signal, the second measurement signal, and the third measurement signal in the first embodiment.

As illustrated in FIG. 7, background noise is superimposed on each measurement signal. The background noise contains electrical background noise in addition to background noise in the optical system.

In a case where a single microbial particle in the sample water 101 is irradiated with the excitation light, the first measurement signal shows a single large pulse due to the autofluorescence of the flavin group increased by ultraviolet light irradiation at the preceding-stage irradiation section 2. The second measurement signal shows a relatively-small pulse. Note that the fluorescence wavelength peak of the autofluorescence substance whose autofluorescence is increased by ultraviolet light irradiation at the preceding-stage irradiation section 2 is not within the second wavelength range. However, due to broad fluorescence characteristics of the flavin group or other autofluorescence substances (e.g., the folate group), the second measurement signal also shows the pulse at the same timing. Moreover, the third measurement signal also shows a pulse due to the scattered light corresponding to the particle size of the microbial particle at the same timing.

In a case where a single non-microbial particle in the sample water 101 is irradiated with the excitation light, the first measurement signal and the second measurement signal show pulses due to the fluorescence of the non-microbial particle. Note that these pulses are extremely small. Thus, the levels of the first measurement signal and the second measurement signal are less likely to exceed the threshold. That is, the fluorescence intensity of the non-microbial particle is not increased even by ultraviolet light irradiation at the preceding-stage irradiation section 2. Thus, the pulses due to the fluorescence of the non-microbial particle are small and less detectable. Then, the third measurement signal shows a pulse due to the scattered light corresponding to the particle size of the non-microbial particle.

The counting processing section 45 continuously compares the levels of the first measurement signal, the second measurement signal, and the third measurement signal as described above with thresholds Th1 to Th3.

When the levels of the first measurement signal and the second measurement signal each exceed the thresholds Th1, Th2 and the pulse height value Vpeak1 (i.e., the local maximum value) of the first measurement signal is larger than the pulse height value Vpeak2 of the second measurement signal, the counting processing section 45 counts a single microbial particle.

That is, in a case where a single microbial particle in the sample water 101 is irradiated with the excitation light, the level of the first measurement signal and the level of the second measurement signal each exceed the thresholds Th1, Th2, and the pulse height value Vpeak1 of the first measurement signal is larger than the pulse height value Vpeak2 of the second measurement signal. Thus, such a single microbial particle is counted.

On the other hand, in a case where a single non-microbial particle in the sample water 101 is irradiated with the excitation light, the fluorescence intensity of the non-microbial particle is not increased as illustrated in FIGS. 3 and 5. Thus, the first measurement signal and the second measurement signal show no significant pulses. Moreover, at least one of the level of the first measurement signal or the level of the second measurement signal does not exceed the threshold Th1, Th2. Thus, such a single non-microbial particle is not counted as the microbial particle. Note that even in a case where the level of the first measurement signal and the level of the second measurement signal each exceed the thresholds Th1, Th2, the pulse height value Vpeak1 of the first measurement signal is less than the pulse height value Vpeak2 of the second measurement signal. Thus, such a single non-microbial particle is not counted as the microbial particle.

Note that in a case where none of the microbial particle and the non-microbial particle in the sample water 101 is irradiated with the excitation light, the level of the first measurement signal and the level of the second measurement signal do not exceed the thresholds Th1, Th2. Thus, no microbial particle is counted.

Further, the counting processing section 45 specifies the size (the particle size) of the single microbial particle based on the pulse height value Vpeak3 of the pulse of the third measurement signal. The pulse of the third measurement signal is obtained at the same timing as obtaining the pulses of the first measurement signal and the second measurement signal due to the above-mentioned single microbial particle.

As described above, according to the first embodiment, the preceding-stage irradiation section 2 irradiates the sample as the fluid with the ultraviolet light at the preceding stage of the microbial particle counter 1. The ultraviolet light is the ultraviolet light with the deep ultraviolet region, the ultraviolet light increasing the fluorescence intensity of the first autofluorescence substance in the microbial particle. Then, the microbial particle counter 1 measures the light intensity in the first wavelength range including the fluorescence wavelength of the first autofluorescence substance and the light intensity in the specific second wavelength range. Based on the measured light intensity in the first wavelength range and the measured light intensity in the specific second wavelength range, the microbial particle is counted in distinction from the non-microbial particle in the fluid.

Specifically in the first embodiment, the second wavelength range is the predetermined wavelength range between the wavelength of the excitation light and the first wavelength range, the predetermined wavelength range not including the fluorescence peak wavelength of an autofluorescence substance, whose fluorescence intensity is increased by the ultraviolet light, in the microbial particle. The microbial particle counter 1 counts the microbial particle in a case where the measured light intensity in the first wavelength range is higher than the measured light intensity in the second wavelength range.

With this structure, the microbial particle is accurately counted in distinction from the non-microbial particle.

That is, as illustrated in FIGS. 2 to 5, in a case where irradiation with the above-mentioned ultraviolet light is not performed, a level relationship between the light intensity of the microbial particle (the bacterium) in the first wavelength range and the light intensity of the microbial particle in the second wavelength range varies according to the type of microbial particle. Thus, this level relationship is sometimes coincident with a level relationship between the light intensity of the non-microbial particle in the first wavelength range and the light intensity of the non-microbial particle in the second wavelength range. Thus, the non-microbial particle and the microbial particle cannot be accurately distinguished from each other. On the other hand, in a case where irradiation with the above-mentioned ultraviolet light is performed, the level relationship between the light intensity of the microbial particle (the bacterium) in the first wavelength range and the light intensity of the microbial particle in the second wavelength range is fixed. Thus, the non-microbial particle and the microbial particle can be accurately distinguished from each other.

Second Embodiment

In a microbial particle counting system according to a second embodiment, a first wavelength range includes, as in the first embodiment, the fluorescence wavelength of a specific autofluorescence substance. In the second embodiment, the first wavelength range includes the fluorescence wavelength of a folate group. The fluorescence peak wavelength of folate and pterin derivative (amethopterin) thereof is about 450 nm. By ultraviolet light irradiation at a preceding-stage irradiation section 2, the pterin derivative (amethopterin) of the folate is generated from the folate. The folate has relatively-low fluorescence intensity. Note that the pterin derivative of the folate has higher fluorescence intensity than that of the folate. Thus, autofluorescence intensity is increased due to ultraviolet light irradiation at the preceding-stage irradiation section 2. Thus, in the second embodiment, the folate group is used as the autofluorescence substance utilized for detection of a microbial particle instead of the flavin group of the first embodiment.

As illustrated in FIGS. 2 and 4, the local maximum value derived from the folate group is also at about 450 nm on the florescence spectrum of the bacterium. Thus, in the second embodiment, the first wavelength range is a wavelength range having a predetermined width including 450 nm. Note that a second wavelength range of the second embodiment is set similarly to the first embodiment. That is, the second wavelength range of the second embodiment is set to between the first wavelength range and excitation light (405 nm in this case).

Note that other structures and operations of the microbial particle counting system according to the second embodiment are similar to those of the first embodiment. Thus, description thereof will be omitted.

Third Embodiment

In a microbial particle counting system according to a third embodiment, a first wavelength range includes the fluorescence wavelength of a specific first autofluorescence substance. A second wavelength range includes the fluorescence wavelength of a specific second autofluorescence substance different from the first autofluorescence substance. The fluorescence intensity of both of the first autofluorescence substance and the second autofluorescence substance are increased due to ultraviolet light irradiation at a preceding-stage irradiation section 2. In the third embodiment, the first autofluorescence substance is a flavin group as described above. The second autofluorescence substance is a folate group as described above. Moreover, in the third embodiment, a counting processing section 45 counts a microbial particle in a case where a difference between measured light intensity in the first wavelength range and measured light intensity in the second wavelength range is within a predetermined range. Note that the first wavelength range and the second wavelength range in the third embodiment are, according to a corresponding autofluorescence substance, set similarly to the first wavelength range of the first embodiment and the first wavelength range of the second embodiment.

Note that a basic structure of the microbial particle counting system according to the third embodiment is similar to that of the first embodiment. Thus, description thereof will be omitted.

Next, counting of the microbial particle in the microbial particle counting system according to the third embodiment will be described.

In a case where a single microbial particle in sample water 101 is irradiated with excitation light, a first measurement signal shows a single large pulse due to autofluorescence of the flavin group increased by ultraviolet light irradiation at the preceding-stage irradiation section 2. A second measurement signal also shows a single great pulse due to autofluorescence of the folate group increased by ultraviolet light irradiation at the preceding-stage irradiation section 2.

The counting processing section 45 continuously compares the levels of the above-mentioned first measurement signal, the above-mentioned second measurement signal, and a third measurement signal with thresholds Th1 to Th3.

When the levels of the first measurement signal and the second measurement signal each exceed the thresholds Th1, Th2 and a difference between the pulse height value (i.e., the local maximum value) of the first measurement signal and the pulse height value of the second measurement signal is within a predetermined range (e.g., equal to or less than a predetermined threshold), the counting processing section 45 counts the single microbial particle.

In a case where a single microbial particle in the sample water 101 is irradiated with the excitation light, the level of the first measurement signal and the level of the second measurement signal each exceed the thresholds Th1, Th2. Further, regardless of the type of microbial particle, both of the pulse height value of the first measurement signal and the pulse height value of the second measurement signal are increased to a similar extent. Thus, a difference between both values is within a predetermined range, and therefore, the single microbial particle is counted.

On the other hand, in a case where a single non-microbial particle in the sample water 101 is irradiated with the excitation light, at least one of the level of the first measurement signal and the level of the second measurement signal does not exceed the threshold Th1, Th2. Thus, the single non-microbial particle is not counted as the microbial particle.

In a case where none of the microbial particle and the non-microbial particle in the sample water 101 is irradiated with the excitation light, the level of the first measurement signal and the level of the second measurement signal do not exceed the thresholds Th1, Th2. Thus, no microbial particle is counted.

Note that other operations of the microbial particle counting system according to the third embodiment are similar to those of the first embodiment. Thus, description thereof will be omitted.

As described above, in the third embodiment, the second wavelength range is the predetermined wavelength range including the fluorescence wavelength of the second autofluorescence substance, whose fluorescence intensity is increased by ultraviolet light, in the microbial particle, the second autofluorescence substance being different from the first autofluorescence substance. The microbial particle counter 1 counts the microbial particle in a case where the difference between the measured light intensity in the first wavelength range and the measured light intensity in the second wavelength range is within the predetermined range.

With this structure, the microbial particle is accurately counted in distinction from the non-microbial particle.

That is, as illustrated in FIGS. 2 and 4, in a case where ultraviolet light irradiation described above is not performed, variation in the difference between the light intensity of the microbial particle (a bacterium) in the first wavelength range and the light intensity of the microbial particle in the second wavelength range is large. For this reason, the non-microbial particle and the microbial particle cannot be accurately distinguished from each other in some cases. On the other hand, in a case where ultraviolet light irradiation described above is performed at the preceding-stage irradiation section 2, the difference between the light intensity in the first wavelength range and the light intensity in the second wavelength range is at a similar level regardless of the type of microbial particle (bacterium). Thus, the non-microbial particle and the microbial particle can be accurately distinguished from each other.

Fourth Embodiment

Figure 8:
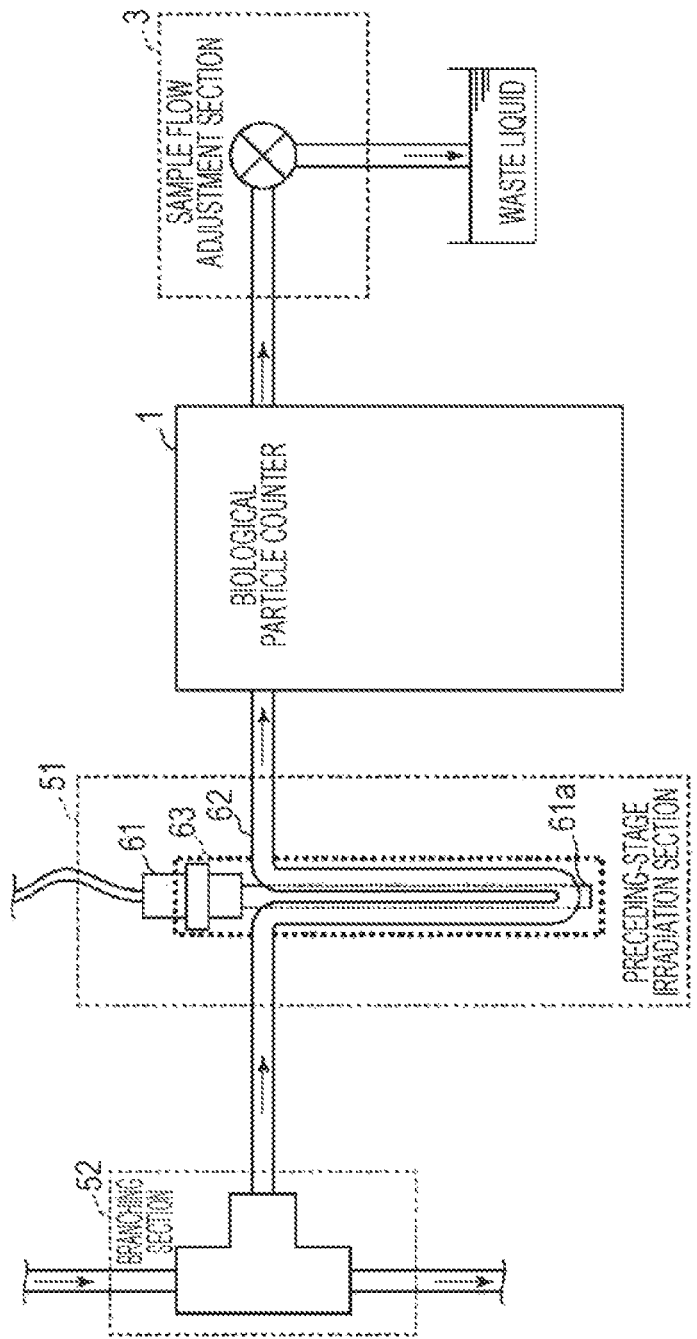
FIG. 8 illustrates a block diagram of a structure of a microbial particle counting system according to a fourth embodiment of the present invention.

FIG. 8 illustrates a block diagram of a structure of a microbial particle counting system according to a fourth embodiment of the present invention. The microbial particle counting system according to the fourth embodiment is a counting system for continuous mode. Thus, the microbial particle counting system according to the fourth embodiment includes a preceding-stage irradiation section 51 for continuous mode. In the fourth embodiment, when a microbial particle counter 1 continuously counts a microbial particle in sample fluid, the preceding-stage irradiation section 51 irradiates, at a stage before the sample flows into the microbial particle counter 1, the sample fluid with ultraviolet light having a deep ultraviolet region, the ultraviolet light being similar to those of the first to third embodiments.

The microbial particle counter 1 in the fourth embodiment is similar to the microbial particle counter 1 in any of the first to third embodiments.

The preceding-stage irradiation section 51 in the fourth embodiment includes a light source 61 configured to emit the ultraviolet light, a flow passage section 62 arranged around the light source 61 and configured such that the sample fluid flows in the flow passage section 62, and a shielding section 63 covering the light source 61 and the flow passage section 62 and configured to reflect or absorb the ultraviolet light The light source 61 is a light source similar to the light source 22 in the first to third embodiments. In the fourth embodiment, the flow passage section 62 is in a tubular shape, such as a quartz tube, having a U-shaped flow passage section extending along a light emitting section 61a of the light source 61. The shielding section 63 is made of a material on which the ultraviolet light is reflectable, such as aluminum or polytetrafluoroethylene (PTFE). The light source 61 and the flow passage section 62 are covered with the shielding section 63, and therefore, the ultraviolet light from the light source 61 is less likely to leak to the outside. In addition, the flow passage section 62 is efficiently irradiated. Note that the shielding section 63 may be a case configured to house the light source 61 and the flow passage section 62. Alternatively, the shielding section 63 may cover the case housing the light source 61 and the flow passage section 62.

Note that when air (external air) around the light source 61 is irradiated with the ultraviolet light from the light source 61, ozone is sometimes generated. In this case, the shielding section 63 is preferably formed into a foil-like shape, and is preferably arranged in close contact with the light source 61 and the flow passage section 62 such that a space between each of the light source 61 and the flow passage section 62 and the shielding section 63 is narrowed. Moreover, a joint portion between the shielding section 63 and the light source 61 and a joint portion between the shielding section 63 and the flow passage section 62 may be sealed such that no ozone generated inside the shielding section 63 leaks to the outside.

Next, counting of the microbial particle in the microbial particle counting system according to the fourth embodiment will be described.

The microbial particle counting system according to the fourth embodiment employs the continuous mode. Thus, the sample flows as the fluid such that ultraviolet light irradiation by the preceding-stage irradiation section 51 and counting of the microbial particle by the microbial particle counter 1 are continuously performed. In this case, the sample is water.

First, the sample water is branched from a main flow passage (e.g., a water pipe) into the preceding-stage irradiation section 51 at a branching section 52 by a sample flow adjustment section 3. In addition, the light source 61 is turned on. Accordingly, the sample water is irradiated with the above-mentioned ultraviolet light during a period in which the sample water is flowing in the flow passage section 62. With this structure, the sample water is irradiated with the above-mentioned ultraviolet light only for predetermined time corresponding to the flow velocity of the sample water and the length of the flow passage section 62. Note that at this point, no aeration is performed for the sample water. Thus, as in the first to third embodiments, the fluorescence intensity of a specific autofluorescence substance in the sample fluid is increased.

Then, the sample water having flowed in the flow passage section 62 of the preceding-stage irradiation section 51 and having been irradiated with the above-mentioned ultraviolet light for the predetermined time flows into the microbial particle counter 1. The microbial particle counter 1 counts the microbial particle in the sample water. At this point, the autofluorescence intensity of the microbial particle is increased, and therefore, the microbial particle in the sample water is accurately counted.

Note that structures and operations of other components in the microbial particle counting system according to the fourth embodiment are similar to the structures and operations of the components of any of the first to third embodiments. Thus, description thereof will be omitted. Note that in the fourth embodiment, the sample flow adjustment section 3 is not necessarily provided as long as a flow rate in the preceding-stage irradiation section 51 and the microbial particle counter 1 can be adjusted based on, e.g., a water pressure at the main flow passage or the branching section 52.

As described above, according to the fourth embodiment, the preceding-stage irradiation section 51 for the continuous mode is provided at a preceding stage of the microbial particle counter 1. The sample fluid is irradiated with the ultraviolet light increasing the intensity of the specific autofluorescence of the microbial particle. With this structure, the microbial particle is accurately counted in real time in distinction from a non-microbial particle.

Fifth Embodiment

In a microbial particle counting system according to a fifth embodiment of the present invention, the preceding-stage irradiation section 51 of the fourth embodiment is changed. FIG. 9 illustrates views of one example of a preceding-stage irradiation section 51 in the microbial particle counting system according to the fifth embodiment of the present invention. FIG. 9(A) illustrates a side view of one example of the preceding-stage irradiation section 51 in the fifth embodiment. FIG. 9(B) illustrates a bottom view of one example of a flow passage section 71 in the fifth embodiment.

In the preceding-stage irradiation section 51 in the fifth embodiment, the flow passage section 71 is provided instead of a flow passage section 62. The flow passage section 71 is an upright cylindrical case. A light source 61 can be housed along a center axis in the flow passage section 71. That is, in the fifth embodiment, sample water having flowed into a lower portion of the flow passage section 71 flows in contact with the light source 61, and flows out of an upper portion of the flow passage section 71. Note that in the fifth embodiment, no aeration is performed for the sample water as in other embodiments.

An inlet port 71a is provided nearby to a bottom surface of the flow passage section 71. An outlet port 71b is provided at a predetermined height position of the flow passage section 71. The outlet port 71*b* is provided above the inlet port 71*a* at the substantially same position as an upper end of a light emitting section 61*a* or a position higher than the upper end. Moreover, the inlet port 71*a* and the outlet port 71*b* are provided, along the tangent to an outer peripheral surface of the flow passage section 71, at predetermined positions apart from the center axis of the flow passage section 71 in a radial direction. With this structure, the sample water having flowed in through the inlet port 71*a* flows in a spiral pattern at the periphery of the light emitting section 61*a* of the light source 61, and then, flows out of the outlet port 71*b*.

Moreover, a shielding section 72 covering the light source 61 and the flow passage section 71 and configured to reflect or absorb the ultraviolet light is placed on the outer peripheral surface of the flow passage section 71. The material of the shielding section 72 is similar to that of the shielding section 63.

Note that structures and operations of other components in the microbial particle counting system according to the fifth embodiment are similar to the structures and operations of the components of the fourth embodiment. Thus, description thereof will be omitted.

Sixth Embodiment

In a microbial particle counting system according to a sixth embodiment of the present invention, a microbial particle counter 1 measures light intensity in a first wavelength range and light intensity in a second wavelength range as described above. In addition, the microbial particle counter 1 measures light intensity in at least one additional wavelength range other than the first wavelength range and the second wavelength range. Moreover, the microbial particle counter 1 counts a microbial particle in distinction from a non-microbial particle in fluid based on the measured light intensity in the first wavelength range, the measured light intensity in the second wavelength range, and the measured light intensity in the additional wavelength range For example, the first wavelength range includes the fluorescence wavelength of a specific first autofluorescence substance similar to that described above. The second wavelength range includes, as in the third embodiment, the fluorescence wavelength of a specific second autofluorescence substance different from the first autofluorescence substance. In a case where the additional wavelength range is the same as the second wavelength range of the first embodiment, when the measured light intensity in the first wavelength range is higher than the measured light intensity in the additional wavelength range and a difference between the measured light intensity in the first wavelength range and the measured light intensity in the second wavelength range is within a predetermined range, the microbial particle is counted. If not, no microbial particle is counted.

For example, the first wavelength range includes the fluorescence wavelength of the specific first autofluorescence substance similar to that described above. The second wavelength range includes, as in the third embodiment, the fluorescence wavelength of the specific second autofluorescence substance different from the first autofluorescence substance. One additional wavelength range is the same (shorter than the first wavelength range) as the second wavelength range of the first embodiment. Another additional wavelength range is longer than the first wavelength range, and as illustrated in, e.g., FIG. 2, is a range including 520 nm as a downward-sloping light intensity portion in a case where the first wavelength range includes a wavelength of 500 nm for a flavin group. When the measured light intensity in the first wavelength range is higher than measured light intensity in the two additional wavelength ranges and the difference between the measured light intensity in the first wavelength range and the measured light intensity in the second wavelength range is within the predetermined range, the microbial particle is counted. If not, no microbial particle is counted.

For example, the microbial particle counter 1 may count the microbial particle in distinction from the non-microbial particle in the fluid, according to light intensity characteristics in association with the wavelength, based on a gradient between the measured light intensity in the first wavelength range and the measured light intensity in the specific second wavelength range (the ratio of a wavelength difference to a light intensity difference between the first wavelength range and the second wavelength range) and on a gradient between the measured light intensity in the first wavelength range and the measured light intensity in the additional wavelength range (the ratio of the wavelength difference to the light intensity difference between the first wavelength range and each additional wavelength range). In this case, when, e.g., all gradients are within corresponding predetermined ranges, the microbial particle is counted. If not, no microbial particle is counted.

Note that structures and operations of other components in the microbial particle counting system according to the sixth embodiment are similar to the structures and operations of other components in any of the first to fifth embodiments. Thus, description thereof will be omitted.

As described above, according to the sixth embodiment, the values of light intensity in three or more wavelength ranges are measured. Based on these light intensity values, the microbial particle is accurately counted in distinction from the non-microbial particle.

Note that various changes and modifications made to the above-mentioned embodiments are obvious to those skilled in the art. These changes and modifications may be made without departing from the gist and scope of the claimed subject matter and degrading intended advantageous effects. That is, these changes and modifications are intended to be included in the claims.

For example, in the first to sixth embodiments, the sample is the liquid. Note that the sample may be gas (e.g., air).

Moreover, in the first to sixth embodiments, the flavin group and the folate group have been described as examples of the autofluorescence substance whose fluorescence intensity is increased in the microbial particle due to ultraviolet light irradiation described above.

Note that other autofluorescence substances may be utilized.

Further, in the first to sixth embodiments, in a case where measurement of the non-microbial particle is not necessary and measurement of the size of the microbial particle is not necessary, the scattered light measurement system (the scattered light selection optical element 35, the light receiving optical system 39, the scattered light receiving device 40, the amplifier 43, and the A/D converter 44) is not necessarily provided. In this case, the light from the detection optical system 34 enters the fluorescence selection optical element 36.

In addition, in the first to sixth embodiments, the preceding-stage irradiation section 2, 51 is separated from the microbial particle counter 1. Note that the preceding-stage irradiation section 2, 51 may be built in the microbial particle counter 1.

Moreover, in the first and second embodiments, the second wavelength range may be longer than the first wavelength range.

INDUSTRIAL APPLICABILITY

The present invention is applicable to counting of a microbial particle, for example.

LIST OF REFERENCE NUMERALS 1 microbial particle counter (one example of microbial particle counter)
2, 51 preceding-stage irradiation section

The invention claimed is:

1. A microbial particle counting system comprising:
a microbial particle counter configured to irradiate fluid with excitation light to detect autofluorescence of a microbial particle in the fluid and count the microbial particle in the fluid; and
a preceding-stage irradiation section provided at a preceding stage of the microbial particle counter and configured to irradiate a sample as the fluid with ultraviolet light,
wherein the ultraviolet light is ultraviolet light having a deep ultraviolet region, the ultraviolet light increasing fluorescence intensity of a first autofluorescence substance in the microbial particle,
the microbial particle counter
measures light intensity in a first wavelength range including a fluorescence wavelength of the first autofluorescence substance and light intensity in a second wavelength range longer than a wavelength of a scattered light from the microbial particle due to an irradiation with the excitation light, and
counts the microbial particle in distinction from a non-microbial particle in the fluid based on the measured light intensity in the first wavelength range and the measured light intensity in the second wavelength range,
the second wavelength range is a predetermined wavelength range between a wavelength of the excitation light and the first wavelength range, the predetermined wavelength range not including a fluorescence peak wavelength of an autofluorescence substance, whose fluorescence intensity is increased by the ultraviolet light, in the microbial particle,
the microbial particle counter counts the microbial particle in a case where the measured light intensity in the first wavelength range is higher than the measured light intensity in the second wavelength range,
the microbial particle counter
(a) counts the microbial particle in distinction from the non-microbial particle in the fluid based on the measured light intensity in the first wavelength range and the measured light intensity in the second wavelength range in a case where the measured light intensity in the first wavelength range and the measured light intensity in the second wavelength range are each higher than predetermined thresholds, and
(b) does not count the microbial particle regardless of the measured light intensity in the first wavelength range and the measured light intensity in the second wavelength range in a case where at least one of the measured light intensity in the first wavelength range or the measured light intensity in the second wavelength range is equal to or lower than the thresholds, and
the predetermined thresholds are each set to values corresponding to an increment of the light intensity in the first wavelength range and an increment of the light intensity in the second wavelength range due to ultraviolet light irradiation.

2. The microbial particle counting system according to claim 1, wherein
the fluid is liquid, and
the second wavelength range is a predetermined wavelength range between the wavelength of the excitation light and a peak wavelength of Raman scattered light from the liquid, the predetermined wavelength range not including the fluorescence peak wavelength of the autofluorescence substance, whose fluorescence intensity is increased by the ultraviolet light, in the microbial particle.

3. The microbial particle counting system according to claim 1, wherein
the microbial particle counter
measures the light intensity in the first wavelength range and the light intensity in the second wavelength range and light intensity in at least one additional wavelength range other than the first wavelength range and the second wavelength range, and
counts the microbial particle in distinction from the non-microbial particle in the fluid based on the measured light intensity in the first wavelength range, the measured light intensity in the second wavelength range, and the measured light intensity in the additional wavelength range.

4. The microbial particle counting system according to claim 3, wherein the microbial particle counter counts the microbial particle in distinction from the non-microbial particle in the fluid based on a gradient between the measured light intensity in the first wavelength range and the measured light intensity in the second wavelength range and a gradient between the measured light intensity in the first wavelength range and the measured light intensity in the additional wavelength range.

5. The microbial particle counting system according to claim 3, wherein
the microbial particle counter measures the light intensity in the first wavelength range and the light intensity in the second wavelength range and measures light intensity in two additional wavelength ranges other than the first wavelength range and the second wavelength range,
one of the two additional wavelength ranges is shorter than the first wavelength range, and
the other one of the two additional wavelength ranges is longer than the first wavelength range.

6. The microbial particle counting system according to claim 1, wherein
the fluid is liquid, and
the second wavelength range is a predetermined wavelength range between the wavelength of the excitation light and a peak wavelength of Raman scattered light from the liquid, the predetermined wavelength range not including the peak wavelength of the Raman scattered light and the fluorescence peak wavelength of the autofluorescence substance, whose fluorescence intensity is increased by the ultraviolet light, in the microbial particle.

7. A microbial particle counting system comprising:
a microbial particle counter configured to irradiate fluid with excitation light to detect autofluorescence of a microbial particle in the fluid and count the microbial particle in the fluid; and
a preceding-stage irradiation section provided at a preceding stage of the microbial particle counter and configured to irradiate a sample as the fluid with ultraviolet light,
wherein the ultraviolet light is ultraviolet light having a deep ultraviolet region, the ultraviolet light increasing fluorescence intensity of a first autofluorescence substance in the microbial particle,
the microbial particle counter
  measures light intensity in a first wavelength range including a fluorescence wavelength of the first autofluorescence substance and light intensity in a second wavelength range longer than a wavelength of a scattered light from the microbial particle due to an irradiation with the excitation light, and
  counts the microbial particle in distinction from a non-microbial particle in the fluid based on the measured light intensity in the first wavelength range and the measured light intensity in the second wavelength range,
the second wavelength range is a predetermined wavelength range including a fluorescence wavelength of a second autofluorescence substance, whose fluorescence intensity is increased by the ultraviolet light, in the microbial particle, the second autofluorescence substance being different from the first autofluorescence substance, and
the microbial particle counter counts the microbial particle in a case where a difference between the measured light intensity in the first wavelength range and the measured light intensity in the second wavelength range is within a predetermined range.

8. A microbial particle counting method comprising:
a step of irradiating a sample with ultraviolet light at a preceding stage of a microbial particle counter; and
a step of causing the sample as fluid irradiated with the ultraviolet light to flow into the microbial particle counter and irradiating the fluid with excitation light in the microbial particle counter, thereby detecting autofluorescence of a microbial particle in the fluid and counting the microbial particle in the fluid,
wherein the ultraviolet light is ultraviolet light having a deep ultraviolet region, the ultraviolet light increasing fluorescence intensity of a first autofluorescence substance in the microbial particle,
the microbial particle counter
  measures light intensity in a first wavelength range including a fluorescence wavelength of the first autofluorescence substance and light intensity in a second wavelength range longer than a wavelength of a scattered light from the microbial particle due to an irradiation with the excitation light, and
  counts the microbial particle in distinction from a non-microbial particle in the fluid based on the measured light intensity in the first wavelength range and the measured light intensity in the second wavelength range,
the second wavelength range is a predetermined wavelength range between a wavelength of the excitation light and the first wavelength range, the predetermined wavelength range not including a fluorescence peak wavelength of an autofluorescence substance, whose fluorescence intensity is increased by the ultraviolet light, in the microbial particle,
the microbial particle counter counts the microbial particle in a case where the measured light intensity in the first wavelength range is higher than the measured light intensity in the second wavelength range,
the microbial particle counter
  (a) counts the microbial particle in distinction from the non-microbial particle in the fluid based on the measured light intensity in the first wavelength range and the measured light intensity in the second wavelength range in a case where the measured light intensity in the first wavelength range and the measured light intensity in the second wavelength range are each higher than predetermined thresholds, and
  (b) does not count the microbial particle regardless of the measured light intensity in the first wavelength range and the measured light intensity in the second wavelength range in a case where at least one of the measured light intensity in the first wavelength range or the measured light intensity in the second wavelength range is equal to or lower than the thresholds, and
the predetermined thresholds are each set to values corresponding to an increment of the light intensity in the first wavelength range and an increment of the light intensity in the second wavelength range due to ultraviolet light irradiation.

9. A microbial particle counting method comprising:
a step of irradiating a sample with ultraviolet light at a preceding stage of a microbial particle counter; and
a step of causing the sample as fluid irradiated with the ultraviolet light to flow into the microbial particle counter and irradiating the fluid with excitation light in the microbial particle counter, thereby detecting autofluorescence of a microbial particle in the fluid and counting the microbial particle in the fluid,
wherein the ultraviolet light is ultraviolet light having a deep ultraviolet region, the ultraviolet light increasing fluorescence intensity of a first autofluorescence substance in the microbial particle,
the microbial particle counter
  measures light intensity in a first wavelength range including a fluorescence wavelength of the first autofluorescence substance and light intensity in a second wavelength range longer than a wavelength of a scattered light from the microbial particle due to an irradiation with the excitation light, and
  counts the microbial particle in distinction from a non-microbial particle in the fluid based on the measured light intensity in the first wavelength range and the measured light intensity in the second wavelength range,
the second wavelength range is a predetermined wavelength range including a fluorescence wavelength of a second autofluorescence substance, whose fluorescence intensity is increased by the ultraviolet light, in the microbial particle, the second autofluorescence substance being different from the first autofluorescence substance, and
the microbial particle counter counts the microbial particle in a case where a difference between the measured light intensity in the first wavelength range and the measured light intensity in the second wavelength range is within a predetermined range.

* * * * *